United States Patent [19]
Dunaway

[11] Patent Number: 5,931,843
[45] Date of Patent: Aug. 3, 1999

[54] SMALL BEAD TIPPED HEMOSTAT FOR CIRCUMCISIONS AND USE THEREOF

[76] Inventor: William Claude Dunaway, 135 E. Highline Dr., Woodland Hills, Utah 84653

[21] Appl. No.: 08/962,522

[22] Filed: Oct. 31, 1997

[51] Int. Cl.[6] .................................................. A61B 17/32
[52] U.S. Cl. ........................................... 606/118; 606/120
[58] Field of Search ..................... 606/118, 205, 606/207, 210, 157, 211

[56] References Cited

U.S. PATENT DOCUMENTS

| | | | |
|---|---|---|---|
| 3,913,586 | 10/1975 | Baumgarten | 606/205 |
| 4,959,067 | 9/1990 | Muller | 606/190 |
| 5,047,049 | 9/1991 | Salai | 606/205 |
| 5,713,919 | 2/1998 | Lahr | 606/207 |

Primary Examiner—Michael Buiz
Assistant Examiner—Vy Quang Bui
Attorney, Agent, or Firm—Jonathan E. Grant; Grant Patent Services

[57] ABSTRACT

The present invention is directed to a hemostat used in performing infant male circumcisions. The hemostat has a small beaded tip which prevents or limits the possibility of causing an accidental injury. Less trauma is caused during surgery due to the use of the smooth, rounded tip of the invention.

9 Claims, 1 Drawing Sheet

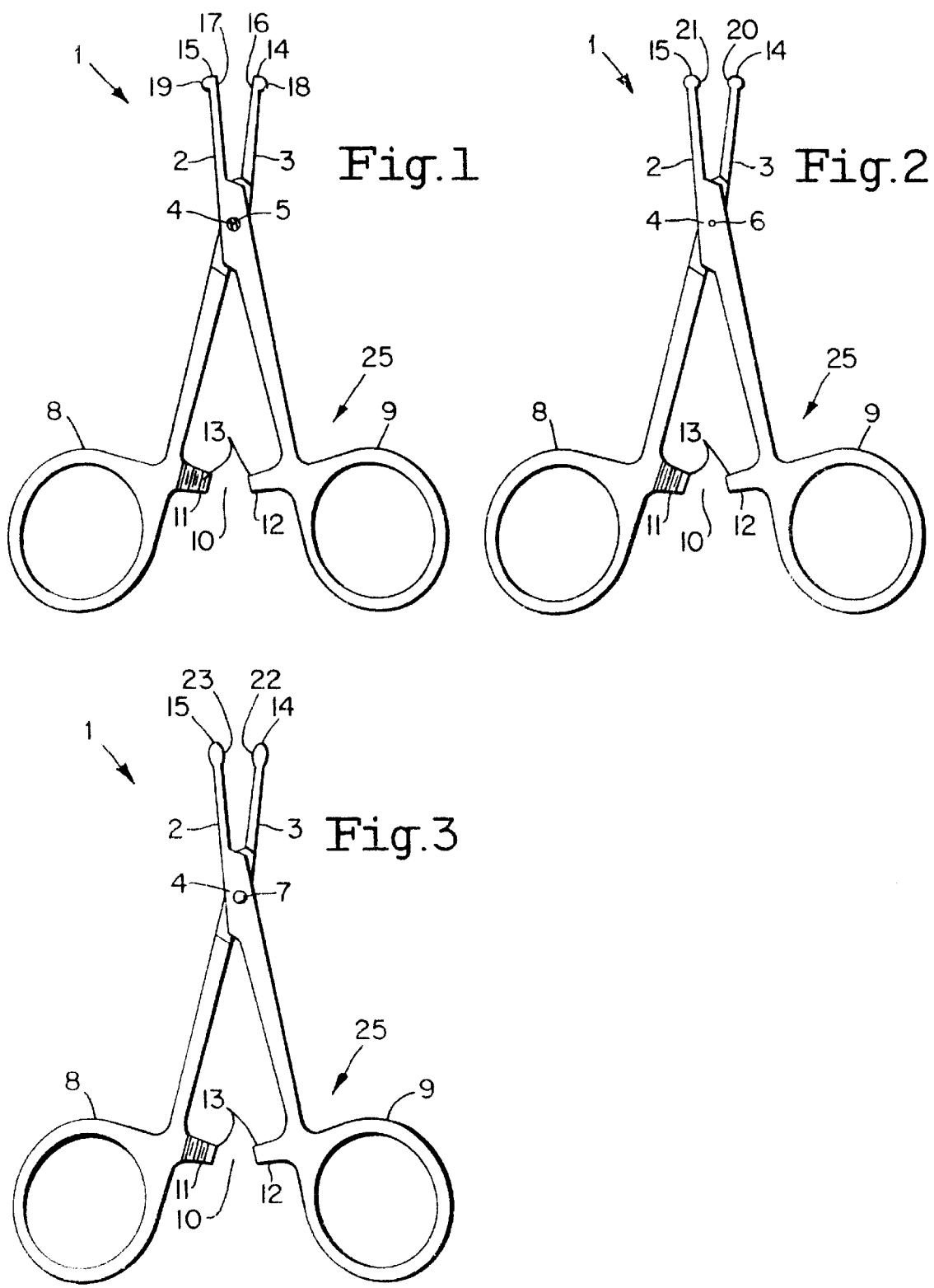

SMALL BEAD TIPPED HEMOSTAT FOR CIRCUMCISIONS AND USE THEREOF

BACKGROUND OF THE INVENTION

1. Field of the Invention

The present invention is directed to a hemostat used in doing infant male circumcisions.

2. Description of the Prior Art

Circumcisions of infant boys remains a very common surgical procedure with approximately 1,200,000 being performed in 1995. In doing most newborn circumcisions, the foreskin is separated from the glans or distal head of the penis using a small "mosquito" hemostat. The foreskin is then removed surgically using a Gomco clamp or Plastibell. A local anesthetic block is applied to the base of the penis before the procedure is started.

At birth, the foreskin is attached firmly to the glans. To separate the foreskin from the glans, two hemostats are attached to a very small segment of foreskin, and gentle traction is made. A hemostat is then inserted between the foreskin and the glans to break the adhesions attaching the foreskin to the glans. The hemostat is gently inserted to the depth of the corona (base of the glans) and the hemostat is then opened and sweeping motions are made in both directions around the glans, thus separating the foreskin from the glans. After the foreskin has been separated from the glans, the foreskin is lifted up to make a "tent". With this tenting, a straight hemostat is firmly clamped to the dorsal aspect of the foreskin in the vertical line of the penis to a depth of about one half of the total length of the foreskin. The straight hemostat is removed and once again with "tenting" the skin, straight scissors are used to carefully cut along the center of the clamp site which has formed hemostasis. The foreskin is now ready to be gently retracted and the bell of the Gomco clamp or Plastibell is placed over the head of the penis and the foreskin is removed.

SUMMARY OF THE INVENTION

In using an existing hemostat, which is pointed, for doing a circumcision, care must be taken not to insert the tip of the instrument into the meatus or opening of the urethra of the penis. Furthermore, when inserting the closed hemostat and then opening it, the glans is subjected to unnecessary abrasion by the pointed end of the hemostat.

By having a small bead tipped hemostat, the possibility of accidently inserting the tip of the hemostat into the meatus is essentially eliminated. Furthermore, less trauma is caused to the surface of the glans because of the smooth, rounded tip of the invention.

BRIEF DESCRIPTION OF THE DRAWINGS

FIG. 1 is an overhead view of the beaded hemostat.

FIG. 2 is an overhead view of another embodiment the beaded hemostat; and

FIG. 3 is an overhead view of yet another embodiment of the beaded hemostat.

DETAILED DESCRIPTION OF THE INVENTION

Referring to the figures, the hemostat 1 includes first and second intersecting arms 2 and 3 interconnected by a pivot point 4. The pivot point 4 positioned at the point of intersection of the two arms 2 and 3 may be comprised of a screw 5, a pin 6, or a rivet 7. At the proximal 5 of each of the arms 2 and 3 of the hemostat 1, there are handles 8 and 9 in the form of loops.

On the inside 10 of the arms 2 and 3, there are preferably locking extensions 11 and 12 having serrated portions 13, extending from each of the arms 2 and 3 to selectively secure the relative positions of arms 2 and 3.

The distal ends 14 and 15 of arms 2 and 3 have bead type structures positioned therein. Specifically, in one embodiment of the invention, the inside surfaces 16 and 17 of arms 2 and 3 are flat, and the outside surfaces 18 and 19 are beaded. In another embodiment of the invention, the inside surfaces 20 and 21 of arms 2 and 3 also beaded or rounded. In yet another embodiment of the invention, the beaded portions 22 and 23 are oval in shape.

In performing a circumcision using the beaded hemostat 1, two beaded hemostats 1 are attached to a very small segment of foreskin, and gentle traction is made. A beaded hemostat 1 is then inserted between the foreskin and the glans to break the adhesions attaching the foreskin to the glans, with one of the beads. The beaded hemostat 1 is gently inserted to the depth of the corona (base of the glans) and the beaded hemostat 1 is then opened and sweeping motions are made in both directions around the glans, thus separating the foreskin from the glans. After the foreskin has been separated from the glans, the foreskin is lifted up to make a "tent". With this tenting, a beaded hemostat 1 is firmly clamped to the dorsal aspect of the foreskin in the vertical line of the penis to a depth of about one half of the total length of the foreskin. The beaded hemostat 1 is removed and once again with "tenting" the skin, straight scissors are used to carefully cut along the center of the clamp site which has formed hemostasis. The foreskin is now ready to be gently retracted and the bell of the Gomco clamp or Plastibell is placed over the head of the penis and the foreskin is removed.

It should be noted that while the hemostat may be suitably made of stainless steel, any suitable materials and manufacturing methods may be utilized. In another embodiment of the invention, the hemostat may be made of plastic, to allow for a disposable hemostat.

Many modifications and variations of the present invention are possible in light of the above teachings. It is, therefore, to be understood within the scope of the appended claims the invention may be protected otherwise than as specifically described.

What is claimed:

1. A beaded hemostat comprising:
    a first intersecting arm having an outside surface and an inside surface;
    a second intersecting arm having an outside surface and an inside surface, said first and second intersecting arms intersecting with each other;
    a pivot point where said first and second intersecting arms intersect;
    a first handle at a proximal end of said first intersecting arm;
    a second handle at a proximal end of said second intersecting arm;
    a bead type structure positioned on the outside surface of a distal end of said first intersection arm and
    a bead type structure positioned on the outside surface of a distal end of said second intersecting arm.

2. The beaded hemostat of claim 1, further comprising a first locking extension extending from an inside surface of said first intersecting arm, and a second locking extension extending from an inside surface of said second intersecting arm, such that said first locking extension and said second locking extension lock together to secure said first intersecting arm and said second intersecting arm in a fixed position.

3. The beaded hemostat of claim 2, wherein said first locking extension and said second locking extension each have serrated portions.

4. The beaded hemostat of claim 1, wherein said first handle and said second handle are in the form of loops.

5. The beaded hemostat of claim 1, wherein the inside surface of the distal end of said first intersecting arm is flat, and the inside surface of the distal end of said second intersecting arm is flat.

6. The beaded hemostat of claim 1, wherein said beaded structure is rounded.

7. The beaded hemostat of claim 1, wherein said beaded structure is oval shaped.

8. A method of performing a circumcision, comprising the steps of:

attaching two beaded hemostats to a segment of a foreskin, said beaded hemostat comprising a first intersecting arm having an outside surface and an inside surface;

a second intersecting arm having an outside surface and an inside surface, said first and second intersecting arms intersecting with each other;

a pivot point where said first and second intersecting arms intersect;

a first handle at a proximal end of said first intersecting arm;

a second handle at a proximal end of said second intersecting arm;

a bead type structure positioned on the outside surface of a distal end of said first intersection arm; and a bead type structure positioned on the outside surface of a distal end of said second intersecting arm;

inserting another beaded hemostat between the foreskin and glans to break adhesions attaching the foreskin to the glans, with one of the beads of said hemostat, the beaded hemostat being gently inserted to a depth of the corona;

opening one of the beaded hemostat;

making sweeping motions with said opened beaded hemostat in both directions around the glans, thus separating the foreskin from the glans;

lifting the foreskin with the beaded hemostat forming a tent;

firmly clamping a beaded hemostat to a dorsal aspect of the foreskin in a vertical line of the penis;

removing the beaded hemostat and tenting the skin, cutting with along the center of the clamp site which has formed hemostasis; and retracting the foreskin.

9. A beaded hemostat comprising:

a first intersecting arm having an outside surface and an inside surface;

a second intersecting arm having an outside surface and an inside surface, said first and second intersecting arms intersecting with each other;

a pivot point where said first and second intersecting arms intersect;

a first handle at a proximal end of said first intersecting arm;

a second handle at a proximal end of said second intersecting arm;

a semispheric structure integrally positioned on the outside surface at a tip of a distal end of said first intersection arm; and a semispheric structure integrally positioned on the outside surface at a tip of a distal end of said second intersecting arm.

\* \* \* \* \*